(12) United States Patent
Liebovitz et al.

(10) Patent No.: US 9,904,769 B2
(45) Date of Patent: Feb. 27, 2018

(54) SYSTEMS AND METHODS FOR PROVIDING A USER ENGAGEMENT PLATFORM TO SUPPORT CLINICAL DECISIONS

(71) Applicant: Northwestern University, Evanston, IL (US)

(72) Inventors: David Liebovitz, Chicago, IL (US); Andrew Naidech, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/729,340

(22) Filed: Jun. 3, 2015

(65) Prior Publication Data

US 2015/0356262 A1    Dec. 10, 2015

Related U.S. Application Data

(60) Provisional application No. 62/008,817, filed on Jun. 6, 2014.

(51) Int. Cl.
*G01N 33/48*  (2006.01)
*G06F 19/00*  (2018.01)
*G06G 7/58*   (2006.01)

(52) U.S. Cl.
CPC ................. *G06F 19/345* (2013.01)

(58) Field of Classification Search
None
See application file for complete search history.

(56) References Cited

U.S. PATENT DOCUMENTS

| | | |
|---|---|---|
| 2005/0055243 A1 | 3/2005 | Arndt et al. |
| 2012/0232918 A1 | 9/2012 | Mack et al. |
| 2013/0024206 A1 | 1/2013 | Hughes et al. |
| 2013/0106864 A1 | 5/2013 | Boyer et al. |
| 2013/0267792 A1 | 10/2013 | Petersen et al. |
| 2013/0275151 A1 | 10/2013 | Moore et al. |
| 2013/0325512 A1 | 12/2013 | Kim et al. |

*Primary Examiner* — Eric S Dejong
(74) *Attorney, Agent, or Firm* — Neal Marcus

(57) ABSTRACT

Systems and methods are disclosed for providing a user engagement platform to support clinical decisions. The user engagement platform is a point of care decision support platform for inpatients in an emergency department (ED), an intensive care unit (ICU), or other medical care department or facility that services patients with critical care needs. The user engagement platform is configured to receive and process data parameters obtained from a patient electronic health record (EHR), identify abnormalities based on such data parameters, prompt a user (e.g., clinician or other healthcare professional such as a nurse) to consider conditions common in ICU or ED patients that could result in patient death and update the patient EHR based on such user input.

27 Claims, 11 Drawing Sheets

DASHBOARD   PATIENT LIST   GUIDELINES

−TEST HOSPITAL

SELECT DEPARTMENT

ICU
PATIENTS IN UNIT: 5
WITH CRITICAL STATUS: 3
WITH WARNING STATUS: 1
NICU
PATIENTS IN UNIT: 0
WITH CRITICAL STATUS: 0
WITH WARNING STATUS: 0

FIND PATIENT

FIG. 7

SYSTEMS AND METHODS FOR PROVIDING A USER ENGAGEMENT PLATFORM TO SUPPORT CLINICAL DECISIONS

CROSS-REFERENCE TO RELATED APPLICATIONS

This application claims priority to U.S. provisional application No. 62/008,817, filed Jun. 6, 2014, entitled "System and Method for Providing a User Engagement Platform to Support Clinical Decisions", which is incorporated by reference herein.

FIELD OF THE INVENTION

The present invention relates to systems and methods for providing a user engagement platform to support clinical decisions.

BACKGROUND OF THE INVENTION

Millions of people visit emergency departments (ED) and intensive care units (ICU) every year. The demand for ED and ICU services are projected to grow rapidly during the next decade as the growth in the elderly population increases. The ability of critically ill patients to receive adequate care depends upon a number of factors, including the availability of highly trained health care professionals and an adequate budget to compensate such professionals. Over the years, many hospitals have reduced budgets for various departments. Therefore, many of the EDs and ICUs do not have sufficient funds to hire an adequate number of professionals to address the needs of such ED and ICU patients. Consequently, many EDs and ICUs are understaffed.

In the ED or ICU, patients present a myriad of symptoms or abnormalities, many of which are associated with several common, yet serious conditions. Unless these conditions are properly identified and addressed in a timely manner, the conditions could quickly result in a patient's death. Surprisingly, many ED and ICU and health care professionals fail to identify these conditions despite the professional's experience and background. Acute lung injury and sepsis are examples of conditions that routinely go undiagnosed. The health care professional shortage and inadequate hospital electronic systems are the primary reasons for such breakdowns.

It would thus be advantageous to provide systems and methods that will overcome the problems described above.

SUMMARY OF THE INVENTION

Systems and methods are disclosed for providing a user engagement platform to support clinical decisions.

In accordance with an embodiment of the present disclosure, a system is disclosed for providing a user engagement platform to support clinical decisions. The system comprises a memory, wherein data parameters relating to one or more organs of a patient are stored in the memory, and one or more processors in communication with the memory, wherein the one or more processors are programmed to evaluate the data parameters to identify abnormalities in the one or more organs, wherein the evaluating includes comparing first and second data parameters relating to an organ of the one or more organs.

In accordance with another embodiment of the present disclosure, a system is disclosed for providing a user engagement platform to support clinical decisions. The system comprises a memory, wherein data parameters relating to one or more organs of a patient are stored in the memory and one or more processors in communication with the memory, wherein the one or more processors are programmed to evaluate the data parameters to identify abnormalities in the one or more organs, wherein the evaluating includes comparing a first data parameter relating to an organ to a threshold.

In accordance with another embodiment of the present disclosure, a system is disclosed for providing a user engagement platform to support clinical decisions. The system comprises a data storage to store a database, wherein data parameters pertaining to one or more organs of a patient are stored in the observation database, and one or more servers coupled to the data storage, wherein the one or more servers are programmed to execute one or more computer program modules for evaluating the patient data parameters to identify abnormalities in the one or more organs, wherein a first module of the one or modules when executed perform a method, the method comprising comparing first and second data parameters relating to an organ, and generating a difference value between first and second data parameters.

In accordance with another embodiment of the present disclosure, a computer-implemented method is disclosed for providing a user engagement platform to support clinical decisions, wherein the method is implemented in one or more servers programmed to execute the method, the method comprising reading, with the one or more servers, first and second EHR data parameters relating to an organ from a patient, comparing, with the one or more servers, the first and second EHR data parameters, wherein comparing generates a difference value between the first and second data parameters; and identifying, with the one or more servers, an abnormality with respect to the organ if the difference value exceeds a threshold.

In accordance with another embodiment of the present disclosure, a computer-implemented method is disclosed for providing a user engagement platform to support clinical decisions, wherein the method is implemented in one or more servers programmed to execute the method, the method comprising: reading, with the one or more servers, first and second EHR data parameters relating to an organ of a patient, comparing a first data parameter relating to an organ to a threshold, and identifying an abnormality in the organ if the first data parameter exceeds a threshold.

In accordance with an embodiment of the present disclosure, a computer readable medium is disclosed for storing a computer program providing a user engagement platform to support clinical decisions, the computer program comprising instructions, which when executed by one or more processors, perform the steps of reading first and second EHR data parameters relating to an organ of a patient, comparing the first and second EHR data parameters, generating a difference value between the first and second EHR data parameters, and identifying an abnormality with respect to the one or more organs if the difference value exceeds a threshold.

In accordance with another embodiment of the present disclosure, a computer readable medium is disclosed storing a computer program providing a user engagement platform to support clinical decisions, comprising instructions stored thereon, which when executed by one or more processors perform the steps of reading an EHR data parameter relating to an organ of a patient, comparing the data parameter to a threshold, and identifying an abnormality with respect to the organ if the EHR data parameter exceeds the threshold.

In accordance with another embodiment of the present disclosure, a system is disclosed for providing a user engagement platform to support clinical decisions, wherein the system includes a memory for storing a plurality of parameters relating to one or more organs of a patient electronic health record (EHR) and one or more processors in communication with the memory, wherein the one or more processors are programmed to receive patient EHR data from an EHR system, parse EHR data parameters to extract data parameters, and map parsed data parameters to observation parameters automatically to create a mapping configuration file.

In accordance with yet another embodiment of the present disclosure, a computer-implemented method is disclosed for providing a user engagement platform to support clinical decisions, wherein the method is implemented in one or more servers programmed to execute the method, the method comprising reading, by the one or more servers, first and second EHR data parameters relating to an organ from a patient, comparing, by the one or more servers, the first and second EHR data parameters, determining, by the one or more servers, a rate of change between the first and second EHR parameters to detect an abnormal condition of the organ.

BRIEF DESCRIPTION OF THE DRAWINGS

FIG. 7 depicts an example home screen of a user interface generated by the user engagement platform to support clinical decisions of FIG. 2.

DETAILED DESCRIPTION OF THE INVENTION

Figure 1:
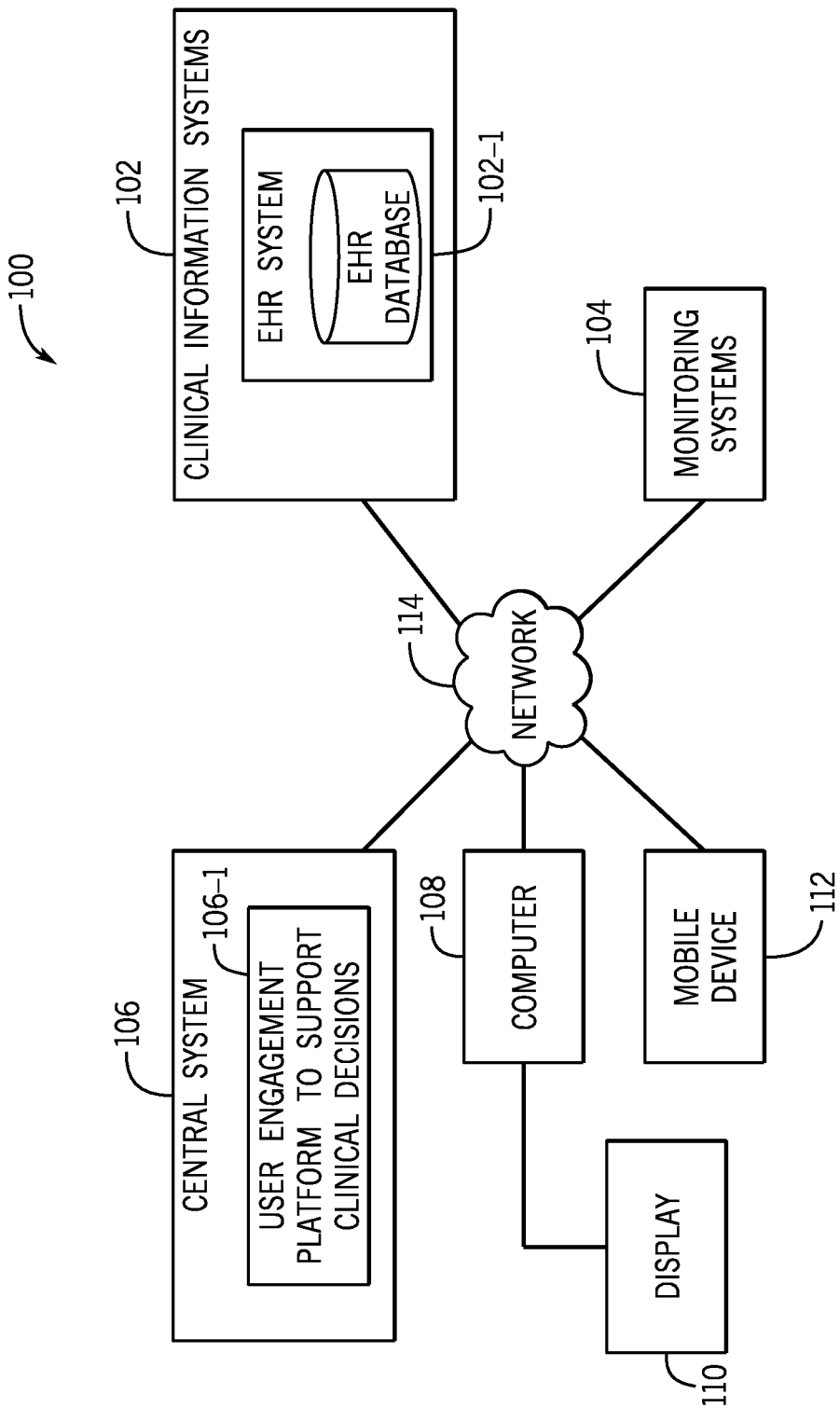
FIG. 1 depicts a block diagram illustrating an example system in which a user engagement platform for supporting clinical decisions operates.

FIG. 1 depicts a block diagram illustrating an example system 100 in which a user engagement platform to support clinical decisions operates. In particular, system 100 is typically a facility system that may include one or more facilities. In the case of multiple facilities, these facilities can be remotely located from one another and/or can be located at a common location or site (e.g., separate departments in a common building). Each facility can be a medical care system, for example, that includes one or more hospitals, clinics, physician offices and the like as known to those skilled in the art. System 100 may be a system other than a facility system as known to those skilled in the art.

In this example, system 100 incorporates clinical information system (CIS) 102, patient monitoring systems 104, central system 106, computer 108, display 110 and mobile device 112. System 100 also includes many other systems (not shown) as known to those skilled in the art such as an administration system, registrations system, billing system, human resource system, procurement system (to name a few). As discussed in detail below, computer 108 and mobile device 112 communicate with CIS 102, monitoring systems 104 and central system 106 through network 114. Network 114 may comprise a local area network (LAN), a wide area network (WAN), a wireless LAN (WLAN), Internet or combinations of the above.

CIS 102 includes electronic health records (EHR) system 102-1. EHR system 102-1 is a system dedicated to collecting, storing, manipulating and making available clinical information important to the delivery of patient care to individuals or groups of patients as known to those skilled in the art. An electronic health record or EHR (also known or referred to as an electronic medical record (EMR)) is a digital version of a paper chart that typically contains a patient's medial history as known to those skilled in the art. EHR system 102-1 incorporates an EHR database wherein patient EHRs are stored. The EHR database is shown as part of EHR system 102-1, but those skilled in the art know that the EHR database may alternatively be implemented externally from EHR system 102-1. EHR system 102-1 is preferably a comprehensive system that covers virtually every facet of clinical information pertinent to the patient, but those skilled in the art know that EHR system 102-1 may alternatively be limited in scope to a single area of clinical information. EPIC Corporation and Cerner Corporation both market several EHR systems for commercial use.

As known to those skilled in the art, CIS 102 may include, or be ancillary to, several other systems such as a cardiology system, an operative system, pulmonary system, neurology system, laboratory system and an intensive care system (to name a few). Data from EHR system 102-1 and any other data from CIS 102 are communicated to central system 106 via network 114. CIS 102 comprises one or more servers that support the execution of software applications and data acquisition, storage, processing, modification and distribution (e.g., EHR and other clinical information) through CIS 102. These servers incorporate several components as described in more detail below.

Monitoring systems 14 are systems for monitoring physiological characteristics or parameters of one or more patients and generate data based on such characteristics. The data is communicated to CIS 102 via network 114 whereby EHR system 102-1 collects and processes the data and then stores it to an EHR associated with a patient in the EHR database as known to those skilled in the art. The data may also be communicated to central system 106 via network 114. This is described in more detail below.

In this example, central system 106 includes user engagement platform to support clinical decisions 106-1 (user engagement platform 106-1). User engagement platform 106-1 is designed to assist a user in making clinical decisions and diagnoses about a patient. In brief, user engagement platform 106-1 is configured to receive and process data parameters obtained from patient EHRs (and other data) in different formats, identify (i.e., alert a user) of various abnormalities based on such data parameters, prompt a user to confirm a condition (diagnosis) and update the patient EHR in accordance with such user input confirmation. This is described in more detail below. Central system 106 comprises one or more servers (including a web server) that support the storage and execution of software applications (e.g., user engagement platform 106-1) and data acquisition, storage, processing, modification and distribution through central system 106. These servers incorporate several components described in more detail below.

In this example, computer 108 is a general-purpose computer, as is known to those skilled in the art. Computer 108 is configured to communicate with CIS 102 via network 114 to enable access to the applications and data that is stored within and managed by CIS 102 (e.g., EHR 12-1). Computer 108 typically includes a keyboard, mouse or trackball, microphone and/or combinations of the above. Computer 108 incorporates several internal components as described in more detail below. In some examples, computer 108 may be a personal computer (e.g., desktop, laptop, or tablet) running various operating systems (e.g., Microsoft Windows, Linux or Apple OS). Although a single computer is depicted in the example system (architecture) and described herein, it is contemplated that more than one computer can communicate with CIS 102 (and monitoring system 14). Computer 108 may be installed anywhere within system 100 such as, for example, an intensive care unit (ICU), emergency unit or cardiology department. Alternatively, computer 108 may be installed outside of system 100. Communication between computer 108 and CIS 102 is achieved remotely via network 114 or alternatively through a direct connection.

Display 110 is display, as is well known in those skilled in the art. Display 110 coupled directly to computer 108 and configured to display information received from computer 108. Display 110 includes, but is not limited to, a thin film transistor (TFT), liquid crystal display (LCD) or an organic light emitting diode (OLED) display.

Mobile device 112, as is well known to those skilled in the art, is configured to communicate wirelessly with and access content from central system 106, CIS 102 or any other systems, over network 114 through a carrier network (e.g., Verizon, Sprint, T-Mobile, AT&T) or available WIFI networks. Mobile device 112 may be a mobile phone, smartphone, tablet, personal digital assistant (PDA), laptop and and/or appropriate combinations thereof as known to those skilled in the art. Mobile device 112 incorporates several components described in more detail below including a display for displaying content. While one mobile device is shown in FIG. 1, those skilled in the art know that any number of mobile devices may be used to achieve desired results.

Figure 2:
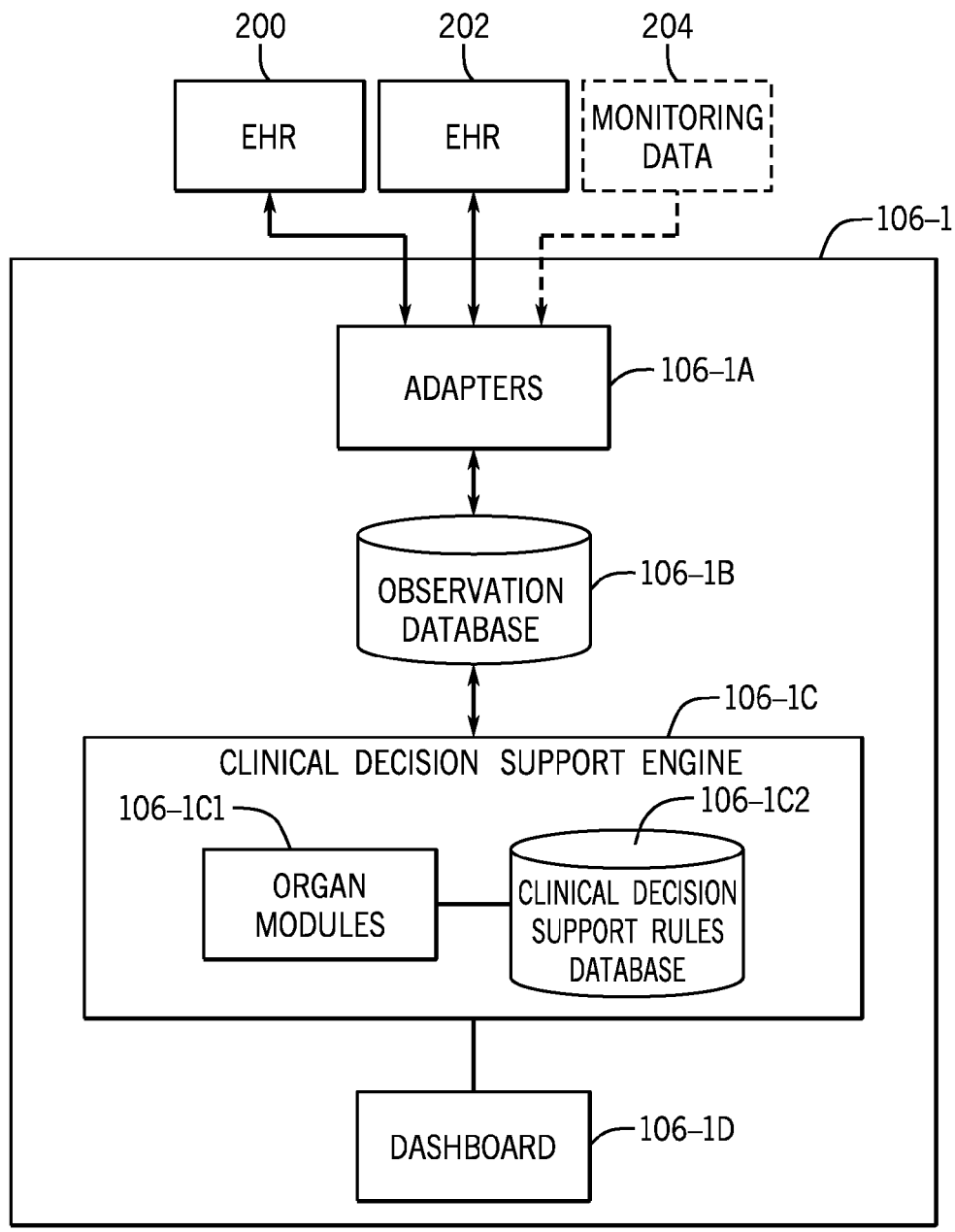
FIG. 2 depicts a block diagram of the user engagement platform to support clinical decisions in FIG. 1.

Reference is made to FIG. 2 wherein a block diagram is depicted of user engagement platform to support clinical decisions 106-1 in FIG. 1. As described above, user engagement platform 106-1 is configured to receive and process data from patient EHRs, alerts the user (e.g., clinician or other healthcare professional) of patient abnormalities, prompt the user to consider and confirm conditions or diagnoses common in ICU or ED patients that could result in death if ignored. There are approximately twenty-four common conditions that form the basis for the presence of the majority of patients in an ICU or ED. Example conditions include a myocardial infarction, hypertension and pneumonia (to name a few). An exemplary list of these conditions or diagnoses is set forth in a table below (at the rear of this disclosure). These conditions are associated with one or more patient medical abnormalities, i.e., parameters stored in and EHR as discussed below. Those skilled in the art know that this list can be expanded to include additional conditions or retracted to reduce the number of conditions.

In particular, user engagement platform 106-1 incorporates several adapters 106-1A, an observation database 106-1B, clinical decision support engine 106-1C (CDS engine 106-1C) and dashboard 106-1D.

Adapters 106-1A are configured to receive, process and adapt, i.e., convert different EHR data structures from various EHR systems (e.g., Cerner, EPIC) into a standard data structure for subsequent processing by CDS engine 106-1C as described in more detail below. EHR data is typically organized and stored according to one of several standard architectures that enable the data to be exchanged between systems. Examples of the standard architectures include Health Level 7 (HL7), Clinical Document Architecture (CDA), Quality Repository Document Architecture (QRDA) and Custom architectures, as known to those skilled in the art. Each adapter effectively converts a particular data structure created by an EHR system (architecture) into a standard data structure.

In this example, adapters 106-1A receive EHR 200 and EHR 202. EHR system 102-1 is configured to push EHR data to user engagement platform 106-1. Certain data architectures such as HL7 are automatically configured to feed EHR data from an EHR database to user engagement platform 106-1. However, those skilled in the art know that adapters 106-1A may be configured to pull (retrieve) EHR data from the EHR database within EHR system 102-1. In other examples, adapters 106-1A may optionally retrieve data from monitoring systems 104 directly if desired. This is shown in dotted lines in FIG. 2. Adapters 106-1A are also configured to transfer user entered data parameters in order to update a patient EHR as described in more detail below.

Figure 3:
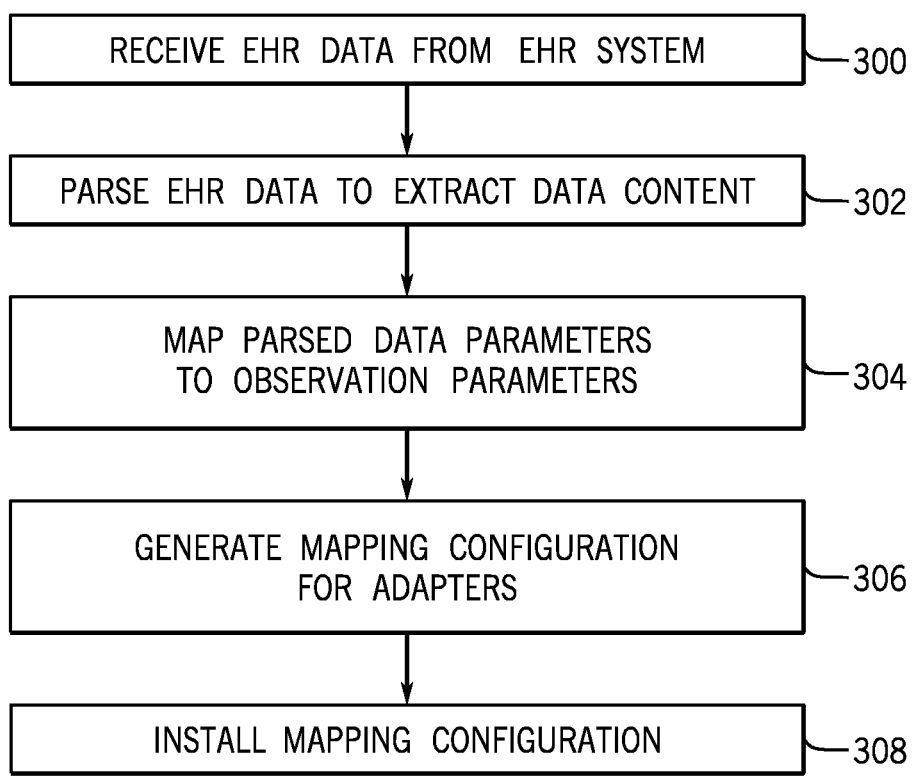
FIG. 3 depicts an example process for creating a mapping configuration file for the adapters shown in FIG. 2.

Adapters 106-1 incorporate a mapping configuration file for converting EHR data into data that can be used by CDS engine 106-1C. This mapping configuration file is a set of mapping rules or instructions for properly mapping EHR data into data used by CDS engine 106-1C. Reference is made to FIG. 3 wherein a process is depicted for creating this mapping configuration file. Execution begins at step 300 wherein EHR data is received from an EHR system. The EHR data (parameters) is then parsed to extract specific data content (data parameters) at step 302.

Execution then moves to step 304 wherein the parsed data parameters are mapped to established observation parameters used by CDS engine 106-1C. Examples of established observation parameters include lab codes, vitals (e.g., height, weight) and medications (to name a few). In one example of mapping, standard terminology such as ICD-9 for a diagnosis may be mapped to a known list of codes in adapters 106-1A. Alternatively, mapping may involve direct code mapping. For example, a hospital may use a special code for a diagnosis of diabetes, which will be mapped to a standard code (e.g., ICD-9) or a unit conversion (e.g., convert height in inches into centimeters). Those skilled in the art know that other configurations may be used for mapping parameters.

As for step 304, this mapping may be accomplished manually or automatically as known to those skilled in the art. Once mapping is complete, execution moves to steps 306 and 308 wherein a mapping configuration file is generated and installed within the adapters 106-1A. This mapping configuration file may be created (i.e., configured) well before (pre-configuration) or at the same time user engagement platform 106-1 is installed at a facility system (on site).

The data retrieved from each EHR includes several parameters that are commonly reported or performed. These parameters include (1) vital signs (e.g., heart rate in beats/min, systolic and diastolic blood pressure (BP) in mm Hg, temperature in Fahrenheit, respiratory rate in breaths/min, (2) laboratory studies, (3) administered medications (selected classes, agents), (4) mechanical ventilator settings and supplemental oxygen classes (fiO2, standard settings), and (5) nursing assessments (e.g., delirium screening, alcohol withdrawal screening score, Glasgow Coma Scale). These laboratory studies comprise serum chemistries, complete blood count (e.g., white blood cell (WBC) and differential (% of each WBC type), hemoglobin (HGB), hematocrit, platelet count), cardiac troponin I, microbiology culture results (source and pos./neg.), urinalysis (presence of blood, WBC or casts) and arterial blood gas results (pH, PCO2, pO2, fiO2). Other data may also be retrieved to achieve desired results. These parameters will be used to identify abnormalities with respect to patient organs.

Observation database 106-B, as is known to those skilled in the art, is a database for storing the data adapted (i.e., converted) by adapters 106-1A and subsequently used by CDS engine 106-1C. Observation database 106-1B enables data transmission to and from adapters 106-1A and CDS Engine 106-1C.

CDS engine 106-1C is configured to retrieve and process data from observation database 106-1B and generate data and images for display by display 110. In particular, CDS engine 106-1C comprises a set of organ modules 106-1C1, each of which includes one or more algorithms that identifies abnormal organ system function and generates and causes the display of an alert and an indicator (different screens) representing such abnormal organ system function. Each organ module analyzes one or more "adapted" EHR parameters that are stored in observation database 106-1B to ultimately determine the status (i.e., functioning of) of a particular organ. In this example, organ modules 106-1C1 generates several icons, each of which is associated with a module and represents an organ traditionally covered on medical rounds. That is, these icons (organs) represent a neurology (brain), respiratory (lung), cardiovascular (heart), digestive system (stomach), renal (kidney), infectious disease (thermometer) and hematology (blood drop). As the example demonstrates, an organ may represent any organ or physiological system within the body. User engagement platform 106-1 is scalable to incorporate additional icons or other symbols for other organs. While icons are used in this embodiment, those skilled in the art know that other symbols or text may be used to represent organs.

As indicated above, user engagement platform 106-1 is configured to generate indicators that represent abnormal organ system function determined by organ modules 106-1C1. In this example, the indicator is associated with an icon. An indicator may be in the form of a color, symbol, pop-up message or other insignia representing abnormal organ system function. For example, the brain icon will change from an original color to a different color when user engagement platform 106-1 identifies that a patient has a neurological problem.

Organ modules 106-1C1, each applies at least one rule that acts as a guideline, i.e., a threshold for evaluating an EHR data parameter. These rules are either based on (1) the standard guidelines established by professional organizations, medical literature and/or other publications for identifying and managing common clinical symptoms and/or (2) customized guidelines established by a facility system. For example, the American Thoracic Society has established standard parameters for the identification and management of acute lung injury. Other sources of thresholds include, for example, Medicacriteria.com, which established standard guidelines for renal failure or current medical literature, which established guidelines for Delirium for the Confusion Assessment Method used in an ICU. Alternatively, a facility system may establish customized guidelines for neurologic function (e.g., such as 100 mm Hg instead of 90 mm Hg as the standard guideline established by a professional organization known as the Brain Trauma Foundation). Those skilled in the art know that there are many more standard guidelines available for use. A table appears below (at the rear of this disclosure) that identifies rules associated with conditions (i.e., diagnoses). Those skilled in the art know that this list can be expanded to include additional rules or retracted to reduce the number of rules.

These rules are stored in clinical decision support (CDS) rules database 106-1C2 that is incorporated within CDS engine 106-1C. Each organ module 106-1C1 has access to CDS rules database 106-1C2 as needed. Importantly, user engagement platform 106-1 has a scalable architecture in which modules and/or new rules may be added (or removed or modified) to CDS engine 106-1C. The operation of an exemplary organ module 106-1C1 is described in more detail below with respect to FIG. 4.

User engagement platform 106-1 also comprises dashboard 106-1D. The dashboard constitutes a set of screens or pages for the presentation of patient data including, for example, (1) home screen/page in which a user has a choice of departments, (2) screen/page in which patients are listed along with organ icons, and (3) alerts for abnormalities along with diagnoses. Examples of the dashboard appear in FIGS. 6-9 (described below).

Figure 4:
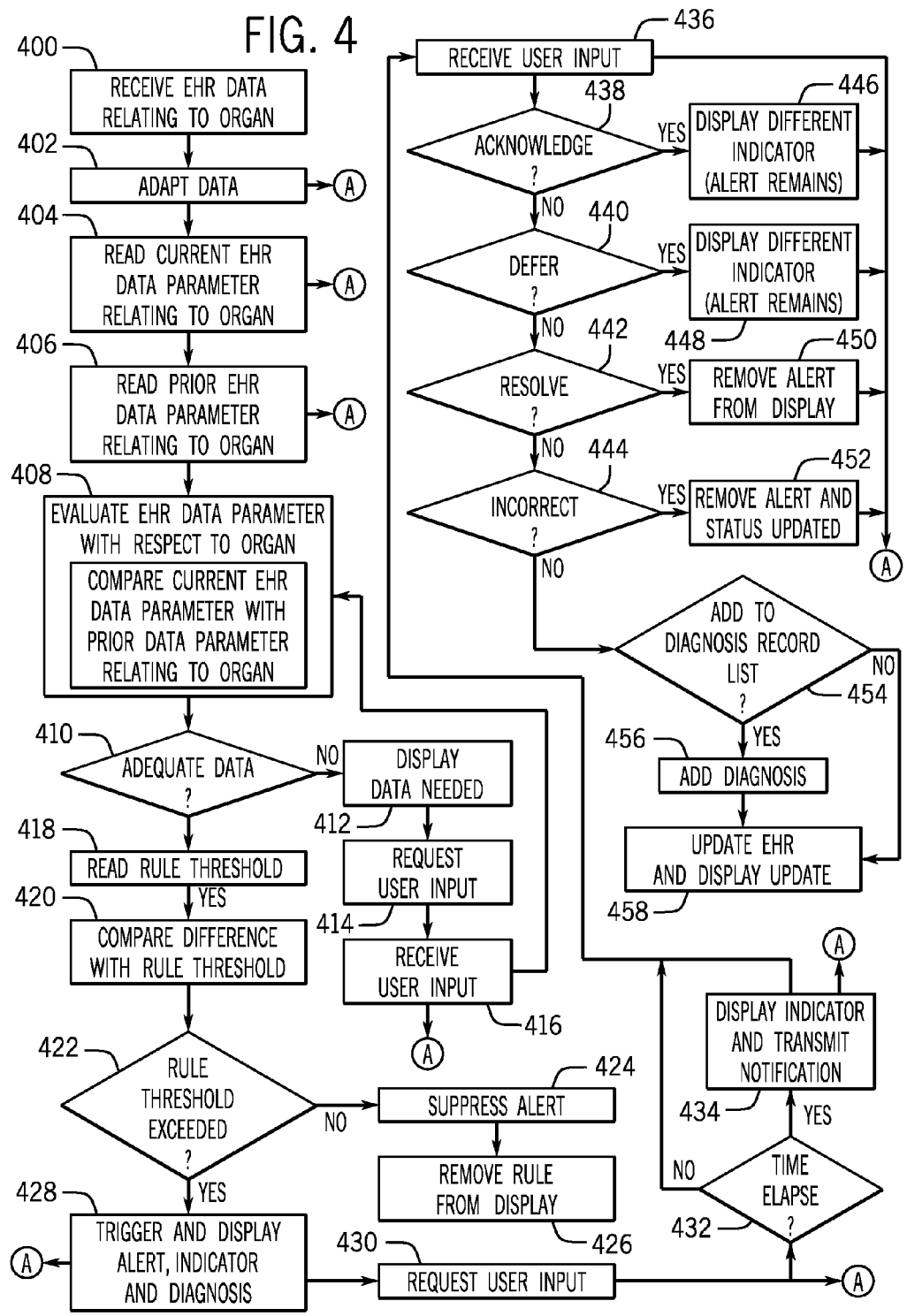
FIG. 4 depicts flowchart steps of an organ module shown in FIG. 2.

Reference is made FIG. 4 wherein flowchart steps are depicted of an exemplary organ module (algorithm) shown in FIG. 2. Execution begins at step 400 wherein EHR data is received relating to one or more patients. Execution moves to steps 402 wherein the EHR data is adapted (i.e., converted) and stored in data architecture (format) for subsequent processing by CDS engine 106-1C. Next, a current (adapted) EHR data parameter and prior (adapted) EHR data parameter relating to an organ of a patient are retrieved and read from observation database 106-1B at steps 404 and 406, respectively. (As indicated, the current and prior EHR data parameters as described are adapted data parameters. However, the adapted EHR data parameters may be referred as "EHR data parameters" or "data parameters" below.) The current data parameter is typically the most recent parameter stored in observation database 106-1B. (Data is also transmitted from steps 402 and 404 and collected for trend analysis at step 600 in FIG. 6 as identified by "A." Data is similarly transmitted at several points in FIGS. 4 and 5 and collected at step 600 in FIG. 6. This is discussed in more detail below with respect to FIG. 6).

Execution then moves to step 408 wherein EHR data with respect to an organ is evaluated to identify abnormalities with respect to that organ. Specifically, current and prior EHR data parameters (measurements taken at different times) relating to the organ are compared. In this comparison, a difference value is obtained between the current and prior parameters (if adequate data is available). Thus, execution moves to decision step 410 wherein it is determined whether there is adequate data to process further steps. In practice, there may not actually be current data parameter(s) related to an organ for making this comparison. For example, a current platelet count may be absent. If not present, the user is prompted to enter additional information. That is, current data is needed and user input is requested at steps 412 and 414, respectively. The user will enter the data parameter(s) at this point. Then execution returns to step 408 wherein the data parameter is evaluated. At the same time, the EHR data stored within the observation database 106-1B and EHR system 102-1 is updated with the entered data parameter (step 458). In this respect, user engagement platform 106-1 actually recognizes that data parameters are not present in the EHR, requests that the user enter such data and updates EHR data. User engagement platform 106-1 accommodates incomplete EHR data and indicates where additional information may be useful. This functionality may be implemented at various points throughout the process in FIG. 4 (and FIG. 5) as known to those skilled in the art. For example, user engagement platform 106-1 may detect absent EHR data when the data is adapted at step 402 or alternatively when current EHR data parameter is read at step 404.

If the answer to decision step 410 is yes, then execution moves to steps 418 and 420 wherein a rule threshold is retrieved, read and compared to the difference value (between data parameters obtained in step 408). The rule threshold is set in accordance with the rules established and stored in CDS rules database 106-1C2 as described above. In this embodiment, the difference value is typically a rate of change (i.e., over time) to detect a movement toward a particular condition.

Once the comparison is performed, execution moves to decision step 422 wherein it is determined whether a parameter has exceeded a rule threshold. If the difference does not exceed the threshold, then an alert of a condition is suppressed. There is thus no abnormality (abnormal parameter) of the organ identified and no active guideline for use at steps 424 and 426, respectively. If the difference value exceeds the threshold, then execution moves to step 428 wherein an abnormality with respect to the organ is identified, and an alert, indicator and diagnosis are triggered (generated) and displayed (as desired per screen).

One example relates to a condition known as acute kidney injury. This example appears as follows:
Parameter$_1$=0.8 mg/decimal creatinine
Parameter$_2$=1.2 mg/decimal creatinine
Rule threshold=30% change over 24 hours In this example, the difference in parameters is 0.4 or 40% over 24 hours. The rate of change (40%) exceeds the rule threshold by 10%. Therefore, user engagement platform 106-1 triggers an indicator, alert and possible diagnosis or condition present. In this example disclosed herein, the indicator is a color change on a renal (kidney) icon. The alert appears on a screen/page accessed by clicking on the icon to obtain details of the organ, alert and condition.

Another example relates to decreased urinary output. This example appears below as follows:
Parameter$_1$=20 ml (at time 1)
Parameter$_2$=25 ml (at time 2)
Parameter$_3$=20 ml (at time 3)
Parameter$_4$=25 ml (at time 4)
Rule threshold=less than 30 ml/hour average over 8 hours The parameters above represent measurements every 2 hours over an 8 period of time. The average is 22.5 ml. This value is less than the 30 ml/hour. Therefore, user engagement platform 106-1 has identified an abnormality with respect to the organ, and generates an alert, indicator and possible condition (diagnosis) for display. Again, in this example, the indicator is a change in color on the renal icon (screen/page with list of icons for multiple patients). If a user desired to view additional details relating to the organ and alert, the user clicks on the organ icon and a new screen appears wherein the additional alert information is displayed relating to the basis for the alert. A diagnosis is also displayed.

At this point, the user input is requested (i.e., prompted for input) at step 430. Execution then moves to decision step 432 wherein it is determined whether a certain predefined time period has elapsed before a user responds (enters data). If the user has responded in time, execution moves to step 436 wherein user input is received. If the user has not responded within the designated time, execution moves to step 434 wherein an indicator is displayed and an escalation notification is transmitted to a user. The indicator may be in the form of a smaller icon imposed on an original icon indicator (threshold exceeded) or any other indicator such as a symbol or representation to ensure that an organ system receives attention. The escalation notification may be a message to the user such as an automatic page, email, text call or other message. Once the indicator is displayed and notification transmitted, execution returns to step 436.

At this point, the user has a few options for addressing this alert. These options are depicted as decision steps 438, 440, 442 and 444. Specifically, once the user input is received at step 436, it is determined whether the user acknowledged the alert at decision step 438. If the user acknowledges the alert, the alert remains but a different indicator (that differs from the other indicators) is displayed at step 446. This indicator is in the form of a different icon color, but other indicators may be used such as a symbol or message for the acknowledged alert. If the user does not acknowledge the alert, then execution moves to decision step 440 wherein it is determined whether the user deferred the alert. If the user defers the alert, the alert remains but a different indicator (different than other indicators) is displayed at step 448. This indicator is in the form of a different color representing the deferred alert. If the user does not defer the alert, execution moves to decision step 442 wherein it is determined whether the user resolved the alert. If the user resolves the alert, the alert disappears from display 110 at step 450. If the user does not resolve the alert, execution moves to decision step 444 wherein it is determined if the alert is incorrect. If user indicates the alert is in error, the alert is removed and the status is updated at step 452. If the alert is not in error, execution moves to decision step 454 wherein the user has the option to add the condition (diagnosis) to the diagnosis record list. If the user chooses to add the diagnosis, it is added at step 456 and execution moves to step 458. If the user does not wish to add it to the diagnosis record, execution moves to step 458 wherein the EHR data is updated and displayed. In this respect, user engagement platform 106-1 is capable of generating output that is fed back into the EHR. For example, if a patient meets the criteria for healthcare associated pneumonia and the user acknowledges this condition, user engagement platform 106-1 is substantiated and the EHR is updated. User engagement platform 106-1 provides two-way interaction with EHRs using standardized protocols.

Figure 5:
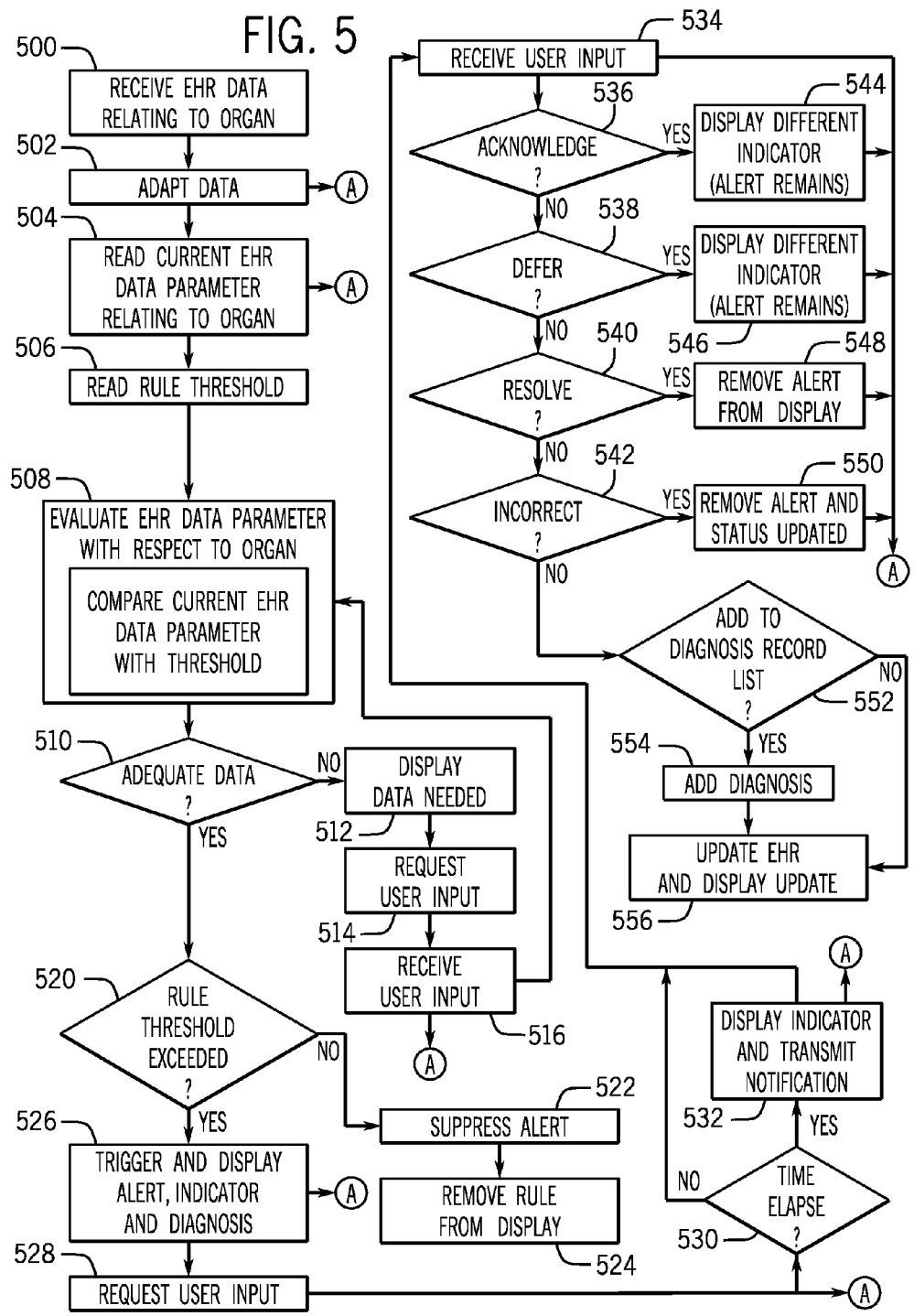
FIG. 5 depicts flowchart steps of an organ module shown in FIG. 2.

FIG. 5 depicts flowchart steps of an organ module shown in FIG. 2. The flowchart in FIG. 5 has a similar format and many of the steps of the organ module in FIG. 4 are the same as in FIG. 5. For example steps 500-504 are the same as depicted in FIG. 4 and described above. Therefore, they will not be repeated here. Execution moves from step 504 to step 506 wherein the rule threshold parameter is read from rules database 106-1C2. At step 508, the current EHR "adapted" data parameter with respect to the organ is evaluated. That is, the current EHR data parameter is compared to the rule threshold. In this respect, the comparison generates a difference value irrespective of time. For example, a current temperature is compared with an established threshold temperature. Execution moves to step 510 wherein it is first determined whether the data is adequate to evaluate the EHR data parameter make the comparison. Data parameters may be absent. If the data parameter is absent, then execution moves to steps 512-514 similar to those corresponding steps in FIG. 4. The display displays that data is needed and prompts the user to enter the information. Entered data is then compared to the rule threshold in step 508.

Similar to FIG. 4, the patient data stored within the observation database 106-1B and EHR system 102-1 is updated with the entered data parameter (step 556). In this respect, user engagement platform 106-1 actually recognizes that data parameters are not present in the EHR, requests that the user enter such data and updates EHR data received from the user. As described above, user engagement platform 106-1 accommodates incomplete EHR data and indicates where additional information may be useful. This functionality may be implemented at various points throughout the process in FIG. 5 as known to those skilled in the art.

Now, if the EHR data parameter does not exceed the threshold, execution moves to step 522 wherein the alert is suppressed (similar to step 424 in FIG. 4). If the EHR data parameter exceeds the rule threshold, execution moves to step 526 wherein an alert, indicator and diagnosis is triggered (generated) and displayed (similar to step 428). Details of these steps are described above. Steps 524, 528, 530, 532, 534, 536, 538, 540, 542, 544, 546, 548, 550, 552, 554 and 556 in FIG. 5 correspond to (are the same as) steps 426, 430, 432, 434, 436, 438, 440, 442, 444, 446, 448, 450, 452, 454, 456 and 458 in FIG. 4. Therefore, the remaining steps in FIG. 4 will not be repeated.

As set forth above, user engagement platform 106-1 will generate and display data that will assist a user in recognizing abnormal patterns more rapidly and potentially lead to earlier diagnosis and treatment. User engagement platform 106-1 is designed to direct a user's attention to important areas of potential concern, to take action including ordering medications, treatments, diagnostics, and surgical/medical therapy.

Figure 6:
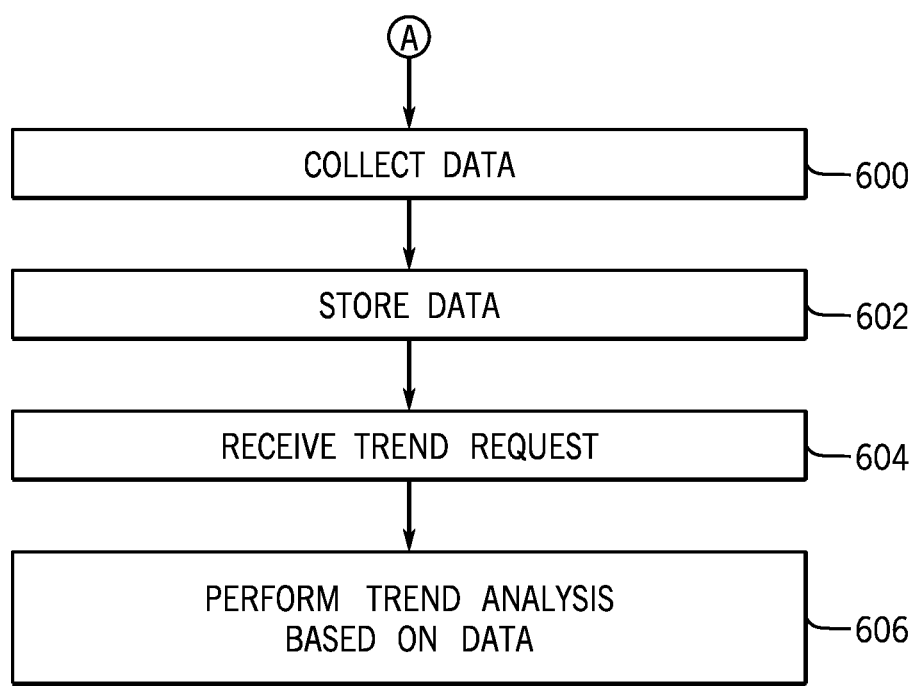
FIG. 6 depicts flowchart of the steps of trend analysis performed on data collected from one or more modules shown in FIG. 2.

FIG. 6 depicts a flowchart of the steps of a trend analysis performed on data collected from one or more modules shown in FIG. 2. In particular, data is collected 600 at several points (e.g., data reading, user entry, in the process shown in FIGS. 4 and 5 as identified by "A." This data is stored at step 602. Once a request is received for trend performance at step 604, trend analysis is performed at the data at step 606. For example, it would be advantageous to keep track and perform analysis of alerts that were incorrectly generated in an effort to make corrections to user engagement platform 106-1.

FIG. 7 depicts a home screen (screenshot of the dashboard) of a user interface generated by user engagement platform 106-1 to support clinical decisions of FIG. 2. The user interface is a dashboard. A user has two department options, both of which are depicted (i.e., ICU and NICU).

Figure 8:
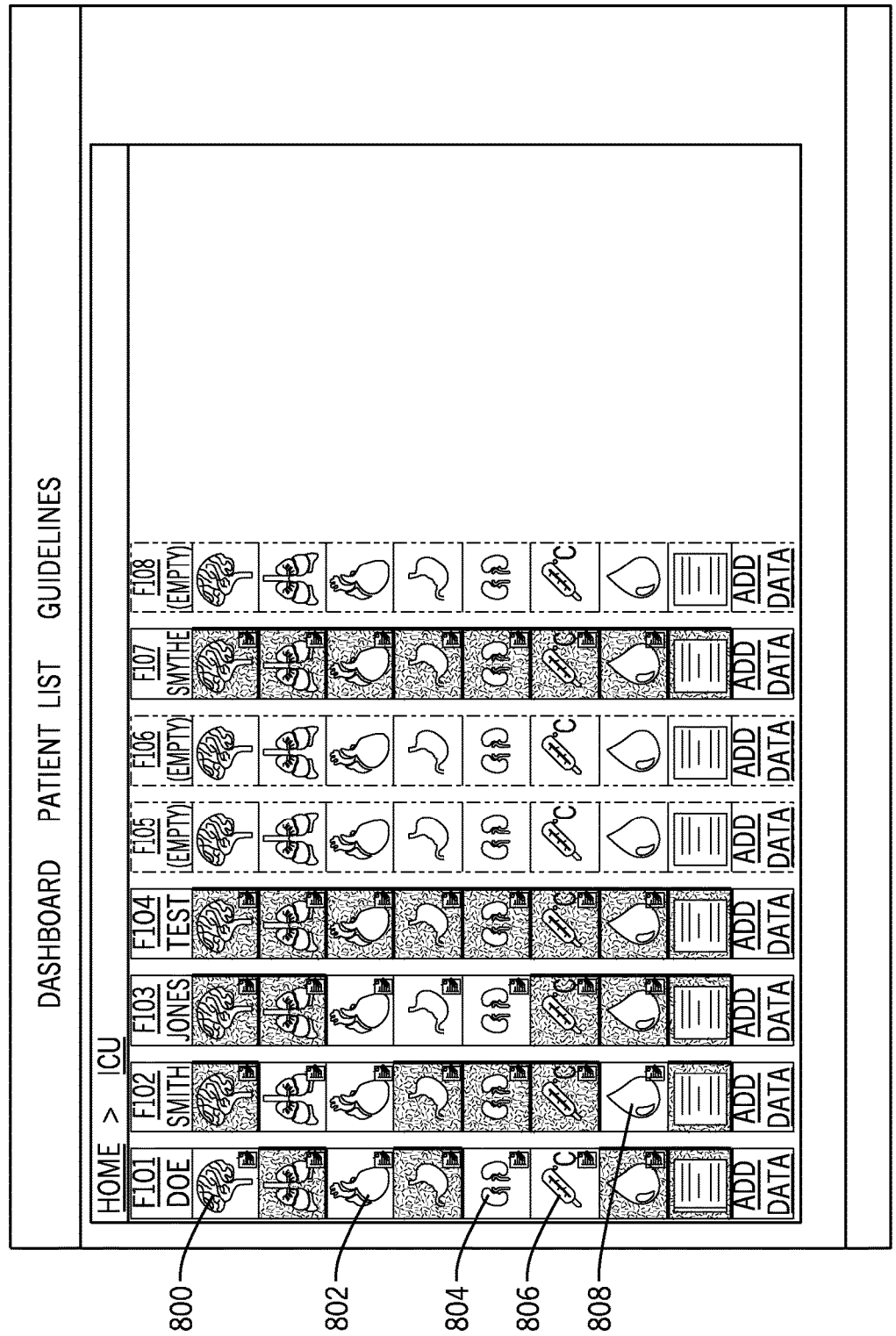
FIG. 8 depicts an example unit screen of a user interface generated by the user engagement platform to support clinical decisions of FIG. 2.

FIG. 8 depicts an example unit screen (of the dashboard) of a user interface generated by user engagement platform 106-1 to support clinical decisions of FIG. 2. In particular, the figure depicts a list of several patient names in an ICU, each of which is represented by several organ icons as described above. In this figure, the sickest patient on service is "Doe." Doe has new critical changes in neurology 800 heart 802, kidney 804 and infection systems 806 (as identified by color change in icon). Patient "Smith" has new blood problems 808 (e.g., low cell count) as identified by a color change in the blood drop icon.

Figure 9:
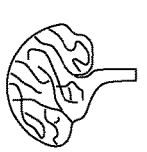
FIG. 9 depicts an example neurological view of a user interface generated by the user engagement platform to support clinical decisions of FIG. 2.

FIG. 9 depicts an example neurological view (of the dashboard) of a user interface generated by user engagement platform 106-1 to support clinical decisions of FIG. 2. In particular, a user will click on the neurologic icon (color change) and user engagement platform 106-1 displays a detailed screen of the neurological alert 900. The alert identifies an "Altered Mental Status" 900 with an abnormality (i.e., Glasgow Coma Scale decrease by at least 2 points). Guidelines are displayed. User options are also displayed including "acknowledge" "defer," "resolve," "alert is incorrect," and/or "Add to Dx List" as described above.

Figure 10:
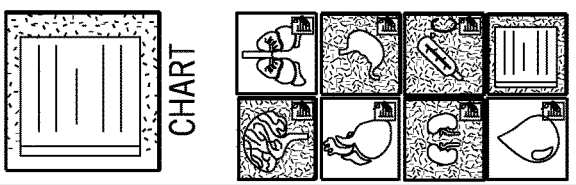
FIG. 10 depicts an example chart of a user interface generated by the user engagement platform to support clinical decisions of FIG. 2.

FIG. 10 depicts an example chart of a user interface generated by user engagement platform 106-1 to support clinical decisions of FIG. 2. In particular, a diagnosis list is displayed for patient Jane Smith. Medical history is also displayed.

Figure 11:
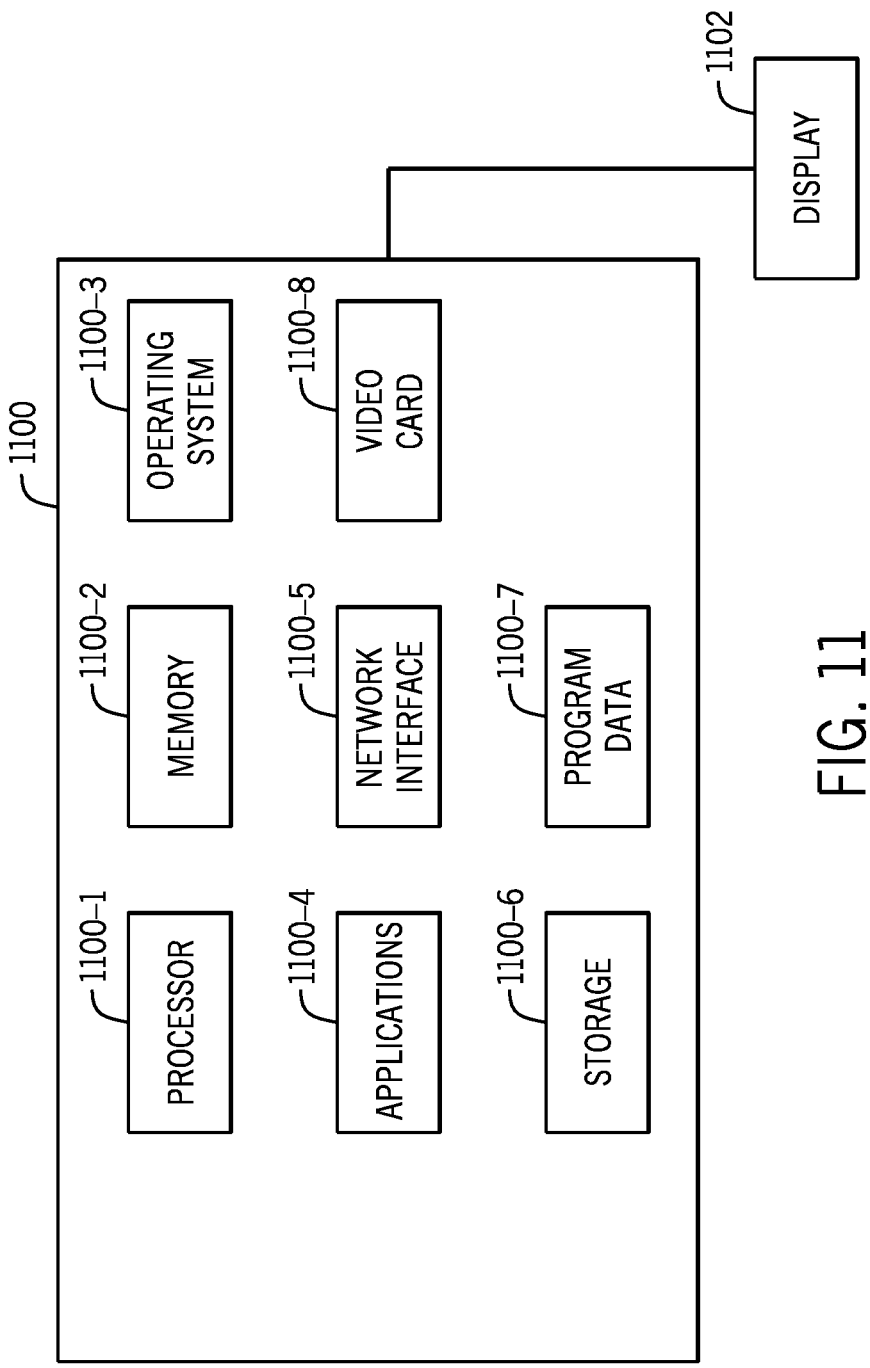
FIG. 11 depicts a general-purpose computer to support the embodiments of the systems and methods disclosed herein.

FIG. 11 depicts a block diagram of a general-purpose computer to support the embodiments of the systems and methods disclosed herein. In a particular configuration, the computer 1100 may be a server as described above with respect to the central system 106, CIS 102 and monitoring systems 104. Computer 1100 may be computer 108 in FIG. 1.

The computer 1100 typically includes at least one processor 1100-1 and system memory 1100-2 (volatile—RAM or non-volatile—Flash or ROM). System memory 1100-2 may include computer readable media that is accessible to the processor 1100-1. The memory 1100-2 may also include instructions for execution by processor 1100-1, an operating system 1100-3 and one or more applications 1100-4 such as Java and a one or more software modules/applications such as user engagement platform 106-1. Computer 1100 will include one or more communication connections such as network interface 1100-5 to enable the computer to communication with other computers over a network, storage 1100-6 such as a hard drives for storing data 1100-7 and other software described above, video card 1100-8 and other conventional components known to those skilled in the art. Computer 1100 typically runs Unix or Microsoft as the operating system and it includes a TCP/IP protocol stack (to communicate) for communication over the Internet (or other network) as known to those skilled in the art. Display 1102 is optionally used.

Although not shown in detail, mobile device 112 includes similar components as the computer 1100 described above. Mobile device 112 preferably incorporates a processor, memory, storage and interface devices as known to those skilled in the art. In particular, the processor is configured to execute instructions and control other components of mobile device 112 in accordance with such instructions. The memory is used for storing instructions. The memory may be volatile and non-volatile memory such as random access memory and read only memory (RAM and ROM). As indicated above, mobile device 112 typically communicates wirelessly but may communicate by wire as desired. Wireless communication is achieved by way of radio unit configured to communicate using radio frequency transmission as known to those skilled in the art. The radio unit incorporates cellular, WIFI and Bluetooth transceivers for communication as known by those skilled in the art. Mobile device 112 also includes display adapter and it is configured to control a display for conveying application process and various activity information, alerts, notifications and the like. The display adapter communicates with a display and a camera. Mobile device 112 also includes storage for storing data and programs as known to those skilled in the art. Device 112 may optionally include input/output adapters as known to those skilled in the art. Mobile device 112 also includes a charging unit for powering device 112. An accelerometer may optionally be incorporated for detecting movement of mobile device 112. Mobile device 112 may include other sensors as known to those skilled in the art. Mobile device 112 also includes an operating system such as iOS, Android or Microsoft Windows Mobile along with other applications including Java etc. as known to those skilled in the art.

It is to be understood that this disclosure teaches examples of the illustrative embodiments and that many variations of the invention can easily be devised by those skilled in the art after reading this disclosure and that the scope of the present invention is to be determined by the claims below.

Conditions/Diagnoses and Rules

| Organ System | Potential Diagnosis/Condition | Rule or Logic |
|---|---|---|
| Cardiovascular | Myocardial infarction | cardiac troponin I >2 mcg/mL |
| | Hypertension, malignant | Systolic BP >200 mm Hg twice |
| | Tachycardia | Heart rate >150 beats/min |
| | Hypotension | Systolic BP <90 mm Hg twice |
| | Bradycardia | Heart rate <40 beats/min |
| Respiratory | Pulmonary embolism | At least readings of heart rate >100 with arterial pCO2 >50 and arterial pH >7.45 |
| | Acute respiratory distress syndrome | If: (arterial partial pressure of oxygen divided by fraction of inspired oxygen) <300, Prompt provider if chest radiograph is consistent with diagnosis. If yes, calculate and suggest tidal volume of 6 mL per kg of ideal body weight (calculated from height) |
| | Readiness of ventilator weaning or extubation | Pressure support mode, pressure support = 5 cm H2O, positive end-expiratory pressure (PEEP) = 5 cm H2O, fraction of inspired oxygen <= 0.4 for at least two hours |
| | Ventilator associated event | Per updated criteria from US Centers for Disease Control. http://www.cdc.gov/nhsn/VAE-calculator/index.htm |
| | Pneumonia | Positive bronchial lavage culture at least 1000 colony forming units |
| Renal/Kidney | Hypovolemia | Central venous pressure <= 3 mm Hg |
| | Risk for acute kidney injury (AKI): | 1.5-fold increase in the serum creatinine, or glomerular filtration rate (GFR) decrease by 25 percent, or urine output <0.5 mL/kg per hour for six hours |
| | AKI: | Twofold increase in the serum creatinine, or GFR decrease by 50 percent, or urine output <0.5 mL/kg per hour for 12 hours |
| | Acute kidney failure: | Threefold increase in the serum creatinine, or GFR decrease by 75 percent, or urine output of <0.3 mL/kg per hour for 24 hours, or anuria for 12 hours |
| Neurologic | Hyponatremia | Serum sodium <130 mEq/L |
| | Hypernatremia | Serum sodium >150 mEq/L |
| | Delirium | Positive delirium screening, such as CAM-ICU or IDSC, or other updated scale. See www.icudelirium.org |
| | Alcohol withdrawal | Clinical Instrument of Withdrawal Assessment (CIWA) >= 15 points |
| | Coma | Glasgow Coma Scale <= 8, or decrease of 2 or more points from baseline |
| Infectious Disease | Bacteremia | Positive blood cultures |
| | Urinary infection | Urinalysis leukocytosis >= 10 WBC and urine culture positive with at least 1000 colony forming units. See also criteria from US CDC |
| | Fever | Temperature at least 101.5 F. or 38.5 C. |
| Hematology | Anemia | Serum hemoglobin <7 mg/dL |
| | Thrombocytopenia | Administration of heparin in the past week and either: 1)decrease in platelet count by 50% from baseline, or <100,000 platelets per microliter |
| | Neutropenia | Absolute neutrophil count (total leukocyte count multiplied by percentage polymorphonuclear cells) <500, if differential obtained |
| Gastrointestinal | Transaminitis | AST or ALT at least three times the upper limit of normal |
| | Pancreatitis | Serum amylase at least three times the upper limit of normal |
| | Cholecystitis | Serum alkaline phosphatase at least three times the upper limit of normal |
| | Malnutrition | Serum albumin <2 mg/dL, or no recorded enteral feeding for three days |

What is claimed is:

1. A system for providing a user engagement platform to support clinical decisions, the system comprising:
   one or more adapters configured to adapt patient electronic health records (EHR) data clinical information systems having different data structures into data having a standardized data structure for subsequent recognition of a condition of a patient, wherein the EHR data includes a plurality of EHR parameters relating to one or more organs of a patient;
   an observation database, wherein data having standardized data structure adapted by one or more adapters are stored;
   a rules database, wherein a plurality of rules for evaluating a plurality of conditions of a patient are stored, each rule associated with a condition of a patient and comprises a threshold value that functions as a guideline for evaluating EHR data parameters relating to one or more organs of a patient to determine whether the condition is present in the patient;
   a plurality of organ modules configured to apply the rules from the rules database to the EHR data parameters from the observation database so as to identify abnormal organ function of a patient,
   one or more processors in communication with the observation database and the rules database; and a memory in communication with the one or more processors, the memory including program instructions executable by the one or more processors that, when executed by the one or processors, cause the one or more processors to:

generate one or more user interfaces for displaying information concerning the one or more organs of the patient, wherein the one or more user interfaces includes (1) a viewing region in which a user may view information relating the one or more organs including alerts, indicators and/or conditions representing abnormalities of the one or more organs and (2) an entry region for a user to input information relating to the organ or more organs;

receive first and second EHR data parameters relating to an organ of the one or more organs from the observation database that have been adapted by the one or more adapters;

evaluate the first and second EHR data parameters to identify abnormalities in the one or more organs, wherein the evaluating includes comparing the first and second EHR data parameters relating to the one or more organs and generating a difference value between the first and second EHR data parameters;

identify at least one abnormality in the one or more organs if the difference value exceeds a threshold value that functions as a guideline for evaluating EHR data parameters relating to one or more organs of a patient; and generate an alert and/or indicator on the one or more user interfaces for display representing the abnormality.

2. The system of claim 1 wherein the memory including program instructions executable by the one or more processors that, when executed by the one or processors, cause the one or more processors to receive a user input via the entry region of the one or more user interfaces relating to the alert and/or indicator.

3. The system of claim 2 wherein the user input acknowledges, defers and/or resolves the alert.

4. The system of claim 3 wherein the memory including program instructions executable by the one or more processors that, when executed by the one or processors, cause the one or more processors to, if the user input acknowledges the alert, update and display via the one or more user interfaces the first and second EHR parameters relating to the organ.

5. The system of claim 4 wherein the memory including program instructions executable by the one or more processors that, when executed by the one or processors, cause the one or more processors to update the rule associated with threshold value in the rules database, thereby updating the condition associated with the rule.

6. The system of claim 3 wherein the one or more user interfaces displays representations of the one or more organs in an alignment from a head to a toe of the patient.

7. A system for providing a user engagement platform to support clinical decisions, the system comprising:
one or more adapters configured to adapt patient electronic health records (EHR) data having different data structures into data having a standardized data structure for subsequent recognition of a condition of a patient, wherein the EHR data includes a plurality of EHR parameters relating to one or more organs of a patient;
an observation database, wherein EHR data having standardized data structure adapted by one or more adapters are stored;

a rules database, wherein a plurality of rules for evaluating a plurality of conditions of a patient are stored, each rule associated with a condition of a patient and comprises a threshold value that functions as a guideline for evaluating an EHR data parameter so as to determine whether the condition is present in the patient;
a plurality of organ modules configured to apply rules from the rules database to the EHR data parameters so as to identify abnormal organ function of a patient;
one or more processors in communication with the observation database and the rules database and a memory in communication with the one or more processors, the memory including program instructions executable by the one or more processors that, when executed by the one or processors, cause the one or more processors to:
generate one or more user interfaces for displaying information concerning the one or more organs of the patient, wherein the one or more user interfaces includes (1) a viewing region in which a user may view information relating the one or more organs including alerts, indicators and/or conditions representing abnormalities with respect to the one or more organs and (2) an entry region for a user to input information relating to the organ or more organs;
receive a data EHR parameter relating to an organ of the one or more organs from the observation database that have been adapted by the one or more adapters;
evaluate the EHR data parameter to identify abnormalities in the one or more organs, wherein the evaluating includes comparing the EHR data parameter relating to an organ to a threshold that functions as a guideline for evaluating the first EHR data parameter to determine whether the condition is present in the patient;
identify at least one abnormality in the one or more organs if the EHR parameter exceeds a threshold value that functions as a guideline for evaluating an EHR data parameter so as to determine whether the condition is present in the patient; and
generate an alert and/or indicator on the one or user interfaces for display representing the abnormality.

8. The system of claim 7 wherein the memory including program instructions executable by the one or more processors that, when executed by the one or processors, cause the one or more processors to receive a user input via the entry region of the user interface relating to the alert and/or indicator.

9. The system of claim 8 wherein the user input acknowledges, defers and/or resolves the alert, if an alert is displayed.

10. The system of claim 8 wherein the memory including program instructions executable by the one or more processors that, when executed by the one or processors, cause the one or more processors to update the rule associated with threshold value in the rules database, thereby updating the condition associated with the rule.

11. The system of claim 7 wherein the one or more user interfaces includes representations of the one or more organs that are in an alignment from a head to a toe of the patient.

12. The system of claim 11 wherein the representations of the one or more organs are color coded.

13. A computer-implemented method for providing a user engagement platform to support clinical decisions, wherein the method is implemented in one or more servers programmed to execute the method, wherein the one or more servers communicate with a computer or mobile device over a network, the method comprising:

providing the one or more servers with (1) one or more adapters configured to adapt patient electronic health records (EHR) data having different data structures into EHR data having a standardized data structure for subsequent recognition of a condition of a patient, wherein the EHR data includes a plurality of parameters relating to one or more organs of a patient, (2) an observation database, wherein EHR data having standardized data structure adapted by one or more adapters are stored, (3) a rules database, wherein a plurality of rules for evaluating a plurality of conditions of a patient are stored, each rule associated with a condition of a patient and comprises a threshold value that functions as a guideline for evaluating an EHR data parameter to determine whether the condition is present in the patient, and (4) a plurality of organ modules configured to apply rules from the rules database on the EHR parameters from the observation database so as to identify abnormal organ function of a patient, reading from the observation database, with the one or more servers, first and second EHR data parameters relating to an organ from a patient;

generating one or more user interfaces for displaying information, on a display connected to the computer or mobile device, concerning the one or more organs of the patient, wherein the one or more user interfaces includes (1) a viewing region in which a user may view information relating the one or more organs including alerts, indicators and/or conditions representing abnormalities of the one or more organs and (2) an entry region for a user to input information relating to the organ or more organs;

evaluating the first and second EHR data parameters to identify abnormalities in the one or more organs, wherein the evaluating includes comparing, with the one or more servers, the first and second EHR data parameters, wherein comparing generates a difference value between the first and second data parameters;

identifying, with the one or more servers, an abnormality with respect to the organ if the difference value exceeds a threshold; and generating, for display on the display or mobile device, an alert and/or indicator on the one or more user interfaces representing the abnormality.

14. The computer-implemented method of claim 13 receive a user input via the entry region of the one or more user interfaces relating to the alert and/or indicator.

15. The computer-implemented method of claim 13 wherein the user input acknowledges, defers and/or resolves the alert.

16. The computer-implemented method of claim 13 if the user input acknowledges the alert, update and display via the display the first and second EHR parameters relating to the organ.

17. The computer-implemented method of claim 15 further comprising updating the rule associated with threshold value in the rules database, thereby updating evaluation of the condition associated with the rule.

18. A computer-implemented method for providing a user engagement platform to support clinical decisions, wherein the method is implemented in one or more servers programmed to execute the method wherein the one or more servers communicate with a computer or mobile device over a network, the method comprising:

providing the one or more servers with (1) one or more adapters configured to adapt patient electronic health records (EHR) data having different data structures into EHR data having a standardized data structure for subsequent recognition of a condition of a patient, wherein the EHR data includes a plurality of parameters relating to one or more organs of a patient, (2) an observation database, wherein EHR data having standardized data structure adapted by one or more adapters are stored, (3) a rules database, wherein a plurality of rules for evaluating a plurality of conditions of a patient are stored, each rule associated with a condition of a patient and comprises a threshold value that functions as a guideline for evaluating an EHR data parameter to determine whether the condition is present in the patient, and (4) a plurality of organ modules configured to apply rules from the rules database on the EHR data from the observation database so as to identify abnormal organ function of a patient;

reading from the observation database, with the one or more servers, first and second EHR data parameters relating to an organ of a patient;

generating one or more user interfaces for displaying information, on a display connected to the computer or a display of the mobile device, concerning the one or more organs of the patient, wherein the one or more user interfaces includes (1) a viewing region in which a user may view information relating the one or more organs including alerts, indicators and/or conditions representing abnormalities of the one or more organs and (2) an entry region for a user to input information relating to the one or more organs;

evaluating the EHR data parameter to identify abnormalities in the one or more organs, wherein the evaluating includes comparing a first data parameter relating to an organ to a threshold value that functions as a guideline for evaluating the EHR data parameter to determine whether the condition is present in the patient;

identifying an abnormality in the organ if the data parameter exceeds the threshold value; and generating, for display via on the display connected to the computer or the display of the mobile device, an alert and/or indicator on the one or more user interfaces representing the abnormality.

19. The computer-implemented method of claim 18 further comprising receiving a user input via the entry region of the one or more user interfaces relating to the alert and/or indicator wherein the identifying includes generating an alert and/or an indicator representing the abnormality.

20. The computer-implemented method of claim 18 further comprising updating the rule associated with threshold value in the rules database, thereby updating evaluation of the condition associated with the rule.

21. A system for providing a user engagement platform to support clinical decisions, the system including one or more servers that communicate with a computer over a network, the system comprising:

a rules database, wherein a plurality of rules for evaluating a plurality of conditions of a patient are stored, each rule associated with a condition of a patient and comprises a threshold value that functions as a guideline for evaluating one or more EHR data parameters to determine whether the condition is present in the patient;

the one or more servers, communicating with the rules database, including a plurality of organ modules configured to apply rules from the rules database on the one or more EHR data parameters to identify abnormal organ function of a patient, the one or more servers configured to execute method steps, the method steps comprising:

generating one or more user interfaces, via a display connected to the computer, for displaying information concerning the one or more organs of the patient, wherein the one or more user interfaces includes (1) a viewing region in which a user may view information relating the one or more organs including alerts, indicators and/or conditions representing abnormalities of the one or more organs and (2) a data entry region for a user to input information relating to the organ or more organs;

receiving a data EHR parameter relating to the one or more organs of the patient;

evaluating the EHR data parameters to identify an abnormalities in the one or more organs, wherein the evaluating includes comparing the EHR data parameter to a threshold value that functions as a guideline for evaluating the first and second EHR data parameters so as to determine whether the condition is present in the patient;

identifying at least one abnormality in the one or more organs if the difference value exceeds the threshold value; and generating for display by the display, an alert and/or indicator on the one or more user interfaces representing the abnormality.

22. The system of claim 21 wherein the method further comprising: update, in response to a user input via the entry region, the rule associated with the threshold value in the rules database, thereby updating the condition associated with the rule.

23. A system for providing a user engagement platform to support clinical decisions, the system including one or more servers that communicate with a computer over a network, the system comprising:

a rules database, wherein a plurality of rules for evaluating a plurality of conditions of a patient are stored, each rule associated with a condition of a patient and comprises a threshold value that functions as a guideline for evaluating one or more EHR data parameters relating to one or more organs of a patient to determine whether the condition is present in the patient;

the one or more servers including a plurality of organ modules configured to apply rules from the rules database on the one or more EHR data parameters to identify abnormal organ function of a patient, the one or more servers configured to execute method steps, the method steps comprising:

generating one or more user interfaces, via a display connected to the computer, for displaying information concerning the one or more organs of the patient, wherein the one or more user interfaces includes (1) a viewing region in which a user may view information relating to the one or more organs including alerts, indicators and/or conditions representing abnormalities of the one or more organs and (2) an entry region for a user to input information relating to the organ or more organs;

receiving first and second data EHR parameters relating to the one or more organs of the patient;

evaluating the first and second EHR data parameters to identify an abnormalities in the one or more organs, wherein the evaluating includes comparing the first and second EHR data parameters relating to the one or more organs and generating a difference value between the first and second EHR data parameters;

identifying at least one abnormality in the one or more organs if the difference value exceeds a threshold value that functions as a guideline for evaluating the first and second EHR data parameters to determine whether the condition is present in the patient;

generating for display by the display, an alert and/or indicator on the one or more user interfaces representing the abnormality; and receiving, via the one or more user interfaces, a user input relating to the alert and/or indicator.

24. A system for providing a user engagement platform to support clinical decisions, wherein the system comprising:

one or more adapters configured to adapt patient electronic health records (EHR) data from clinical information systems having different data structures into EHR data having a standardized data structure for subsequent recognition of a condition, wherein the EHR data includes a plurality of parameters relating to one or more organs of a patient;

an observation database for storing the data having standardized data structure adapted by one or more adapters;

a clinical decision support engine configured to process the data received from the observational database and identify abnormal organ function of a patient;

one or more processors in communication with the observation database; and a memory in communication with the one or more processors, the memory including program instructions executable by the one or more processors that, when executed by the one or processors, cause the one or more processors to:

receive patient EHR data from an EHR system;

parse EHR data parameters having a first structured to extract data parameters, into a format having a standardized data structure; and map parsed data parameters to established observation parameters that are used by the the clinical decision support engine;

automatically create a mapping configuration file based on the mapped parsed data; and install the mapping configuration file in the one or more adapters.

25. A computer-implemented method for providing a user engagement platform to support clinical decisions, wherein the method is implemented in one or more servers programmed to execute the method, the method comprising:

providing the one or more servers with (1) one or more adapters configured to adapt patient electronic health records (EHR) data having different data structures into data having a standardized data structure for subsequent recognition of a condition of a patient, wherein the EHR data includes a plurality of parameters relating to one or more organs of a patient, (2) an observation database, wherein data having standardized data structure adapted by one or more adapters are stored, (3) a rules database, wherein a plurality of rules for evaluating a plurality of conditions of a patient are stored, each rule associated with a condition of a patient and comprises a threshold value that functions as a guideline for evaluating an EHR data parameter to determine whether the condition is present in the patient, and (4) a plurality of organ modules configured to access the rules database and identify abnormal organ function of a patient, reading from the observation database, with the one or more servers, the first and second EHR data parameters relating to an organ from a patient;

generating one or more user interfaces for displaying information, on a display of a computer or mobile device, concerning the one or more organs of the patient, wherein the one or more user interfaces includes (1) a viewing region in which a user may view information relating the one or more organs including alerts, indicators and/or conditions representing abnormalities of the one or more organs and (2) a data entry region for a user to input information relating to the organ or more organs;

evaluating the first and second EHR data parameters to identify abnormalities in the one or more organs, wherein the evaluating includes comparing, with the one or more servers, the first and second EHR data parameters, wherein comparing generates a difference value between the first and second data parameters;

determining, by the one or more servers, a rate of change between the first and second EHR parameters to detect an abnormal condition of the organ; and generating, for display via the computer or mobile device, an alert and/or indicator on the one or more user interfaces representing the abnormality.

26. The method of claim 25 wherein determining includes generating a difference value between the first and second EHR parameters to identify the abnormal condition.

27. The system of claim 23 wherein the one or more servers configured to execute method steps, the method steps comprising in response to the user input, updating the rule associated with threshold value in the rules database, thereby updating evaluation of the condition associated with the rule.

* * * * *